United States Patent [19]

Yoshihara

[11] Patent Number: 4,990,790
[45] Date of Patent: Feb. 5, 1991

[54] METHOD FOR DISCRIMINATING AUTHENTICITY OF A BILL USING POLARIZATION AND AN APPARATUS THEREFORE

[75] Inventor: Kenzou Yoshihara, Kounosu, Japan
[73] Assignee: Nippon Conlux Co., Ltd., Tokyo, Japan
[21] Appl. No.: 413,261
[22] Filed: Sep. 27, 1989
[30] Foreign Application Priority Data Oct. 28, 1988 [JP] Japan ................................ 63-270977

[51] Int. Cl.$^5$ ............................................. G06K 5/00
[52] U.S. Cl. ................................... 250/556; 250/225; 356/369
[58] Field of Search ....................... 250/556, 225, 461.1; 209/534; 377/8; 356/71, 369

[56] References Cited

U.S. PATENT DOCUMENTS

| | | | |
|---|---|---|---|
| 3,496,370 | 2/1970 | Haville et al. | 250/556 |
| 3,497,304 | 2/1970 | Berube | 209/534 |
| 4,250,393 | 2/1981 | Greenaway | 356/71 |
| 4,526,466 | 7/1985 | Sandercock | 356/71 |

Primary Examiner—David C. Nelms
Assistant Examiner—K. Shami
Attorney, Agent, or Firm—Koda and Androlia

[57] ABSTRACT

An apparatus for discriminating the authenticity of a bill put into an automatic vending machine, etc. on the basis of a degree of brilliance of a surface of the bill, comprises two photodiodes for receiving light irradiated from a light-emitting diode and reflected by the bill, and a polaroid filter disposed in front of one of the photodiodes. A differential amplifier or a divider is supplied with output currents from the photodiodes, respectively representing an amount of the reflected light received not through the polaroid filter and containing a polarized component which is produced when the light is reflected on the surface of the bill, and an amount of the reflected light, received through the filter and containing no polarized component, and generates an output voltage indicative of the difference between or the ratio of the output currents, which voltage is compared with a corresponding reference voltage in a comparator whose output assumes a Low-level for a lusterless authentic bill, and a High-level for a brilliant counterfeit bill obtained by color-copying the authentic bill, whereby the authenticity of the bill is accurately discriminated.

20 Claims, 4 Drawing Sheets

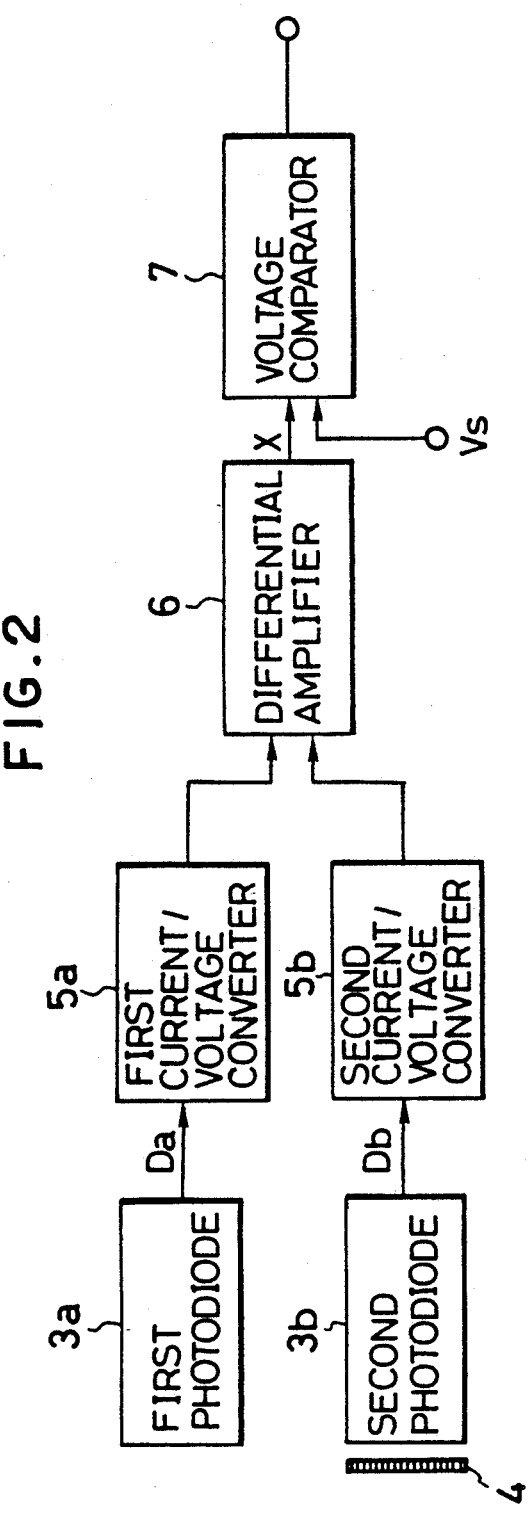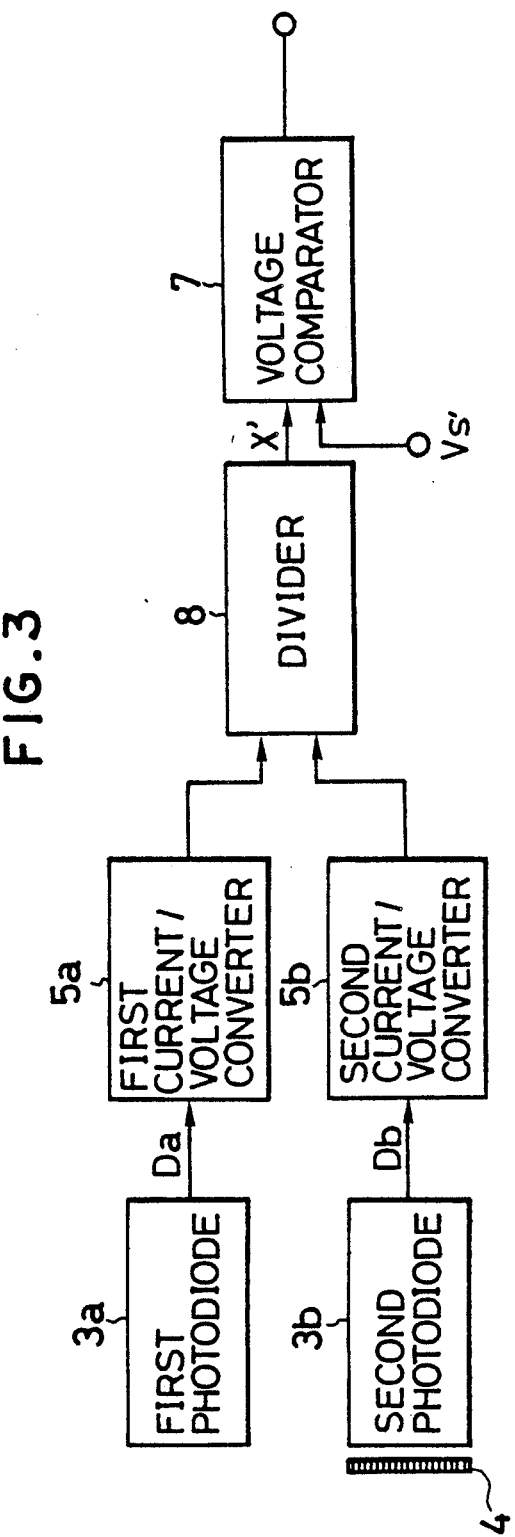

METHOD FOR DISCRIMINATING AUTHENTICITY OF A BILL USING POLARIZATION AND AN APPARATUS THEREFOR

BACKGROUND OF THE INVENTION

The present invention relates to a method for discriminating the authenticity of a bill and an apparatus therefor for use in automatic vending machine, automatic service machine, automatic exchanger, automatic cash dispenser, etc.

An automatic vending machine or the like is required to discriminate the authenticity of a bill put into the machine. To this end, conventionally, the machine is equipped with an apparatus for discriminating the authenticity of a bill, which comprises, for instance, a light source for irradiating light onto the bill, and a light-receiving element for receiving reflected or transmitted light from the bill, and which operates to discriminate the authenticity of the bill on the bass of a level of an output of the light-receiving element. In another prior art (see, Japanese Provisional Patent Publication No. 62-296292), two color components of the reflected light are separately detected, so as to determine a color of the bill on the basis of respective detected levels of the two color components, to thereby discriminate the authenticity of the bill. A still another prior art is known (see, Japanese Provisional Patent Publication No. 62-276685), which is arranged to discriminate an authentic bill from a counterfeit bill obtained by color-copying the authentic bill on the basis of an output of a light-receiving element, which receives a regularly reflected light from a surface of a bill, and that of another light-receiving element which receives an irregularly reflected light therefrom.

However, on one hand, the light source and the light-receiving element change is their characteristics as an ambient temperature varies, and on the other hand, a thrown bill also includes variable factors such as freshness/oldness of the bill, presence/absence of wrinkles and stains in the bill. Accordingly, a difficulty is encountered in setting a reference level in case that discrimination of the authenticity of a bill is effected on the basis of an output of the light-receiving element. Namely, if the reference level is strictly set to a level close to the authentic-bill-side, an authentic bill is sometimes erroneously determined as a counterfeit bill. On the contrary, if the reference level is loosely set to a level close to the counterfeit-bill-side, a counterfeit bill can be erroneously determined as an authentic bill. In this manner, according to prior art, a difficulty arises in eliminating an incorrect discrimination. Particularly, it is difficult to accurately discriminate an authentic bill from a sophisticated counterfeit bill which is obtained by color-copying the authentic bill.

SUMMARY OF THE INVENTION

The object of the present invention is to provide a method for discriminating the authenticity of a bill and an apparatus therefor, capable of carrying out an accurate discrimination of an authentic bill from various counterfeit bills including one produced by color-copying the authentic bill, on the basis of a novel discrimination principle by which the authenticity of the bill is determined in accordance with a difference between a degree of brilliance of a surface of the authentic bill and that of the counterfeit bill, without being adversely affected by a variation of characteristics of a light source and a light-receiving element, the presence of wrinkles, stains in the bill, etc.

According to one aspect of the present invention, a method for discriminating authenticity of a bill is provided, which comprises steps of: (a) irradiating light onto the bill at a predetermined angle of incidence; (b) detecting an amount of reflected light from the bill, said reflected light containing a polarized component which is produced when the light is reflected on a surface of the bill; (c) detecting an amount of the reflected light from which said polarized component is eliminated; and (d) detecting a degree of brilliance of the surface of the bill on the basis of the amount of said reflected light detected by said step (b) and that detected by said step (c), to thereby discriminate the authenticity of the bill.

According to another aspect of the present invention, an apparatus for discriminating authenticity of a bill is provided, which comprises: a light source for irradiating light onto the bill at a predetermined angle of incidence; a first light-receiving element arranged to directly receive reflected light from the bill for generating a first electrical signal which varies in dependence on an amount of the reflected light received by said first light-receiving element; a second light-receiving element arranged to receive the reflected light; a polaroid filter arranged between the bill and said second light-receiving element on a path along which said reflected light is propagated, for eliminating a polarized component of the reflected light which is produced when the light is reflected on a surface of the bill, said second light-receiving element being operable to generate a second electrical signal which varies in dependence on an amount of said reflected light received by said second light-receiving element through said polaroid filter; and a discrimination means for detecting a degree of brilliance of the surface of the bill on the basis of said first and second electrical signals, to thereby discriminate the authenticity of the bill.

According to a further aspect of the present invention, an apparatus for discriminating authenticity of a bill is provided, which comprises: a light source for irradiating light onto the bill at a predetermined angle of incidence; a light-receiving element for receiving reflected light from the bill for generating an electrical signal which varies in dependence on an amount of the reflected light received by said light-receiving element; a polaroid filter arranged to be movable between a first position, located between the bill and said light-receiving element on a path along which said reflected light is propagated, and a second position retreated from said propagation path of said reflected light, said polaroid filter being operable to eliminate a polarized component of the reflected light which is produced when the light is reflected on a surface of the bill; drive means for causing said polaroid filter to move between said first and second positions; and a discrimination means for detecting a degree of brilliance of the surface of the bill on the basis of said electrical signals generated when said polaroid filter assumes said first and second positions, respectively, to thereby discriminate the authenticity of the bill.

BRIEF DESCRIPTION OF THE DRAWINGS

FIG. 2 is a block diagram showing an electrical circuit section of the apparatus of the first embodiment;

FIG. 3 is a view similar to FIG. 2, showing an apparatus according to a second embodiment of the present invention;

DETAILED DESCRIPTION

An apparatus for discriminating the authenticity of a bill, according to a first embodiment of the present invention, is mounted on an automatic vending machine, for instance, and is arranged to discriminate the authenticity of a bill, which is put into the vending machine and delivered to a predetermined location within the discriminating apparatus.

Figure 1:
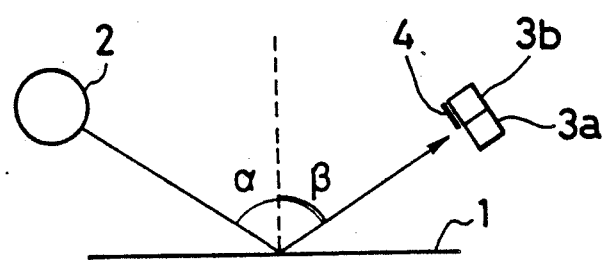
FIG. 1 is a schematic side view showing a positional relationship among a light-emitting diode, two photodiodes, and a polaroid filter of an apparatus for discriminating the authenticity of a bill, according to a first embodiment of the present invention.

Referring to FIGS. 1 and 2, the discriminating apparatus comprises a light source for irradiating light onto a predetermined location on a surface of the thrown bill 1 at a predetermined angle $\alpha$ of incidence, e.g., a light-emitting diode 2 for generating visible light, and first and second light-receiving elements arranged to receive reflected light which is reflected on the surface of the bill 1 at an angle $\beta$ ($=\alpha$) of reflection for generating electrical signals, respectively, each of which varies in dependence on an amount of the reflected light received by a corresponding one of these elements. For instance, the light-receiving elements are comprised of first and second photodiodes $3a$, $3b$ which are formed on a single chip in a manner adjacent to each other. Further, a polaroid filter 4 for preventing a polarized component of the light from passing therethrough, which light is polarized when it is reflected on the bill surface, is disposed at a location in front of the light-receiving face of the second photodiode $3b$, i.e., at a location between the bill surface and the same photodiode on a path along which the reflected light is propagated. The aforementioned angle $\alpha$ of incidence is set to an angle falling within a predetermined angular region, e.g., an angle larger than 45° (about 60° in this embodiment), which angle permits the light to be polarized to a desired degree enough to enable the discriminating apparatus to attain to a desired discriminating performance.

As shown in FIG. 2, the first and second photodiodes $3a$, $3b$ have output terminals respectively connected to input terminals of first and second current/voltage coverters $5a$, $5b$ whose output terminals are connected to two input terminals of a differential amplifier 6, respectively. An output terminal of the amplifier 6 is connected to one input terminal of a voltage comparator 7 having another input terminal to which a reference voltage Vs is applied.

In the following, an operation of the discriminating apparatus constructed as above will be explained.

When a bill 1 is put into the automatic vending machine, a conventional bill delivery unit (not shown) of the discriminating apparatus delivers the bill 1 to a predetermined position (illustrated in FIG. 1) within the discriminating apparatus with the aid of a known sensor system (not shown) of the apparatus, and temporaly holds the bill at that position. Next, a drive circuit (not shown) of the apparatus is operated under the control of the control unit (not shown) provided in the automatic vending machine or the discriminating apparatus, so that the light-emitting diode 2 is turned ON to irradiate a visible light onto the surface of the bill 1 at an angle $\alpha$ of incidence about 60°. Part of the irradiated light is reflected on the surface and within the bill at an angle $\beta$ of reflection and is propagated in the air toward the first and second photodiodes $3a$, $3b$. The remaining part of the irradiated light is absorbed by the bill 1 or passes therethrough. The reflected light is directly received, without a substantial loss, by the first photodiode $3a$ between itself and the bill 1 no optical obstacle is interposed.

Here, the reflection factor of the light on the surface of the bill 1 varies as a function of the degree of brilliance of the bill surface. Accordingly, the reflected light from an authentic bill, which is lusterless, is small in quantity, whereas an amount of the reflected light from a counterfeit bill is large, which bill is obtained by color-copying the authentic bill (hereinafter referred simply to as the counterfeit bill) and is brilliant. Therefore, an output current Da of the first photodiode $3a$ receiving the reflected light from the surface and interior of the bill 1, which current Da varies in dependence on the amount of light received by the same photodiode, has a small value for the authentic bill, whereas it has a large value for the counterfeit bill.

In the other hand, the reflected light directing from the bill surface to the second photodiode $3b$ reaches the polaroid filler 4 disposed in front of the second photodiode, before it reaches the same diode. And, the light from the light-emitting diode 2 is at least partially polarized in the direction parallel to the bill surface, i.e., in the horizontal direction when it is reflected on the surface of the bill 1. The polaroid filter 4 operates to prevent the horizontally polarized component of the reflected light from passing the filter. As a consequence, the amount of the reflected light from which the polarized component thereof is eliminated and which is then received by the second photodiode $3b$, is smaller than the amount of the reflected light directly received by the first photodiode $3a$ and still containing the polarized component. Then, the second photodiode $3b$ produces an output current Db which varies in dependence on the thus reduced amount of the light received by the same photodiode. As mentioned above, in the case of the counterfeit bill, the reflected light from the bill 1 contains therein a large quantity of the polarized component, and hence the output current Db is greatly reduced to have a value considerably less than the output current Da.

The output currents Da, Db from the first and second photodiodes $3a$, $3b$ are converted into corresponding voltages in the first and second current/voltage converters $5a$ and $5b$, respectively, and are applied to the differential amplifier 6. Whereupon, an output voltage from the amplifier 6, corresponding to the difference X ($=Da-Db$) between the output currents Da, Db, is compared with the reference voltage Vs in the comparator 7. As mentioned above, the difference X between the output current Da, indicative of the amount of the reflected light received not through the polaroid filter 4 and containing the polarized component, and the output current Db, indicative of the amount of the reflected light received through the polaroid filter 4 and not containing the polarized component, becomes large for the brilliant counterfeit bill, as compared with the lusterless authentic bill. As a consequence, the output voltage of the amplifier 6 indicative of the difference X assumes a small value for the authentic bill, whereas it assumes a large value for the counterfeit bill. In this respect, the reference voltage Vs is set to an intermediate value between these values. Thus, the output from the comparator 7 assumes a Low-level when the authentic bill is put into the automatic vending machine, whereas it assumes a High-level when the counterfeit bill is put thereinto. In this manner, the output of the comparator 7 assumes a different level between when the authentic bill is thrown and when the counterfeit bill is thrown, to thereby indicate the authenticity of the bill.

As conventionally known, the control unit of the automatic vending machine refers to the level of the output of the comparator 7, and operates in a normal manner when the authentic bill is thrown whereas it operates to return the counterfeit bill to the outside of the machine when the same is thrown.

With reference to FIG. 3, a discriminating apparatus according to the second embodiment of the present invention will be now explained.

As compared with the apparatus of the aforesaid first embodiment, the discriminating apparatus of this embodiment is different in that a divider 8 is employed in stead of the differential amplifier 6 although the other arrangement is the same as that of the aforesaid embodiment. That is, in the present embodiment, the authenticity of the bill 1 is determined on the basis of the ratio of an amount of the reflected light received not through the polaroid filter 4 to that received through the filter rather than the difference between them.

More specifically, the output current Da of the first photodiode 3a, indicative of an amount of the reflected light received by the same photodiode not through the polaroid filter 4 and containing the polarized component, and the output current Db of the second photodiode 3b, indicative of an amount of the reflected light received by the photodiode through the filter 4 and not containing the polarized component, are respectively applied to two input terminals of the divider 8 through the first and second current/voltage converters 5a and 5b, and then an output voltage of the divider 8, indicative of the ratio X' (=Da/Db) of the current Da to the current Db, is compared with a reference value Vs' in the comparator 7.

As explained in the above, the difference between the output currents Da, Db is relatively small for the lusterless authentic bill from which a small amount of surface-reflected light (corresponding to the polarized component of the light) is reflected, and is large for the brilliant counterfeit bill from which a great amount of the surface-reflected light is reflected.

Thus, the ratio X' (=Da/Db) of the current Da to the current Db assumes a value, which is larger than "1" but close to "1", for the authentic bill, whereas it assumes a value which is considerably larger than "1" for the counterfeit bill. The reference value Vs' is set to an intermediate value between them. As a result, the comparator 7 generates an output signal which assumes a Low-level for the authentic bill and a High-level for the counterfeit bill, respectively, to thereby indicate the authenticity of the bill.

Figure 4:
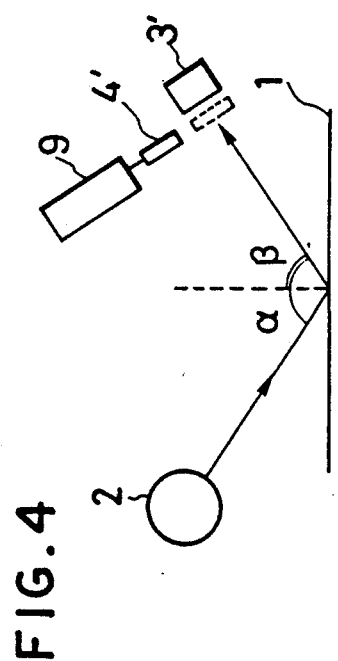
FIG. 4 is a view similar to FIG. 1, showing an apparatus according to a third embodiment of the present invention.
Figure 5:
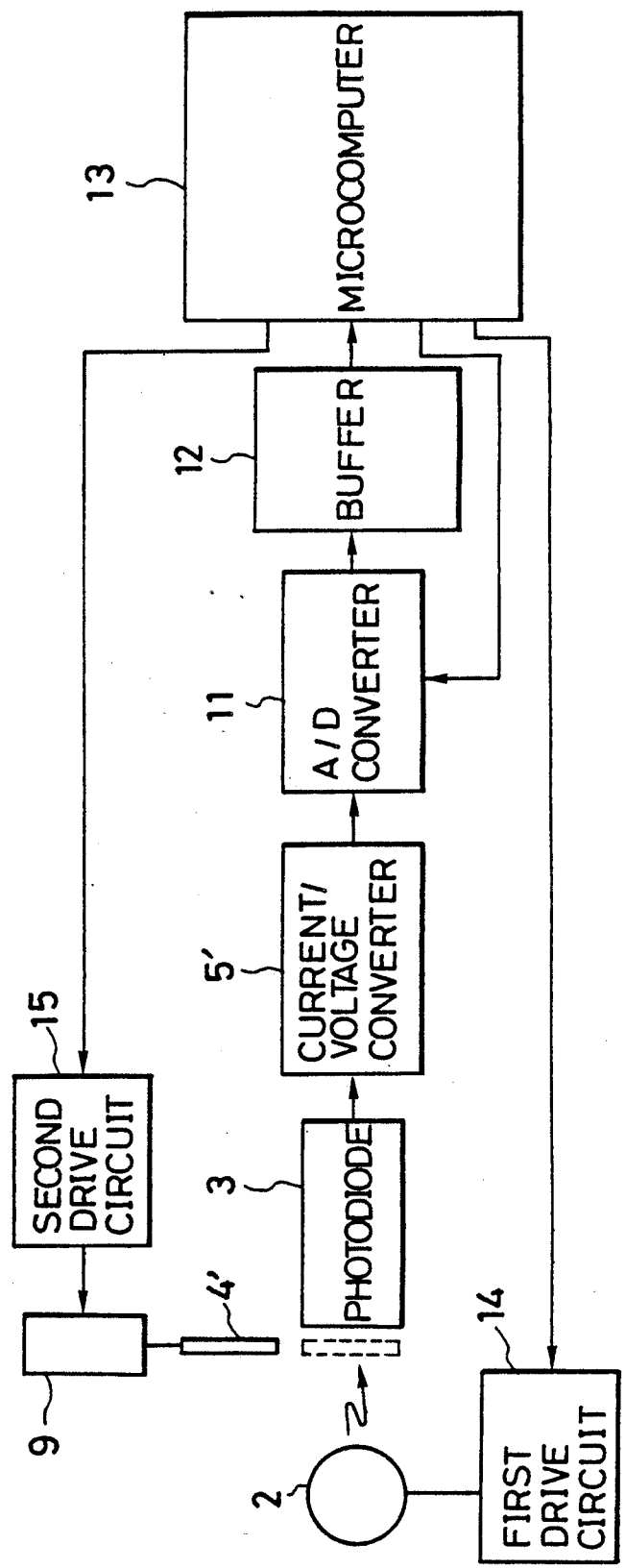
FIG. 5 is a view similar to FIG. 2, showing the apparatus according to the third embodiment.
Figure 6:
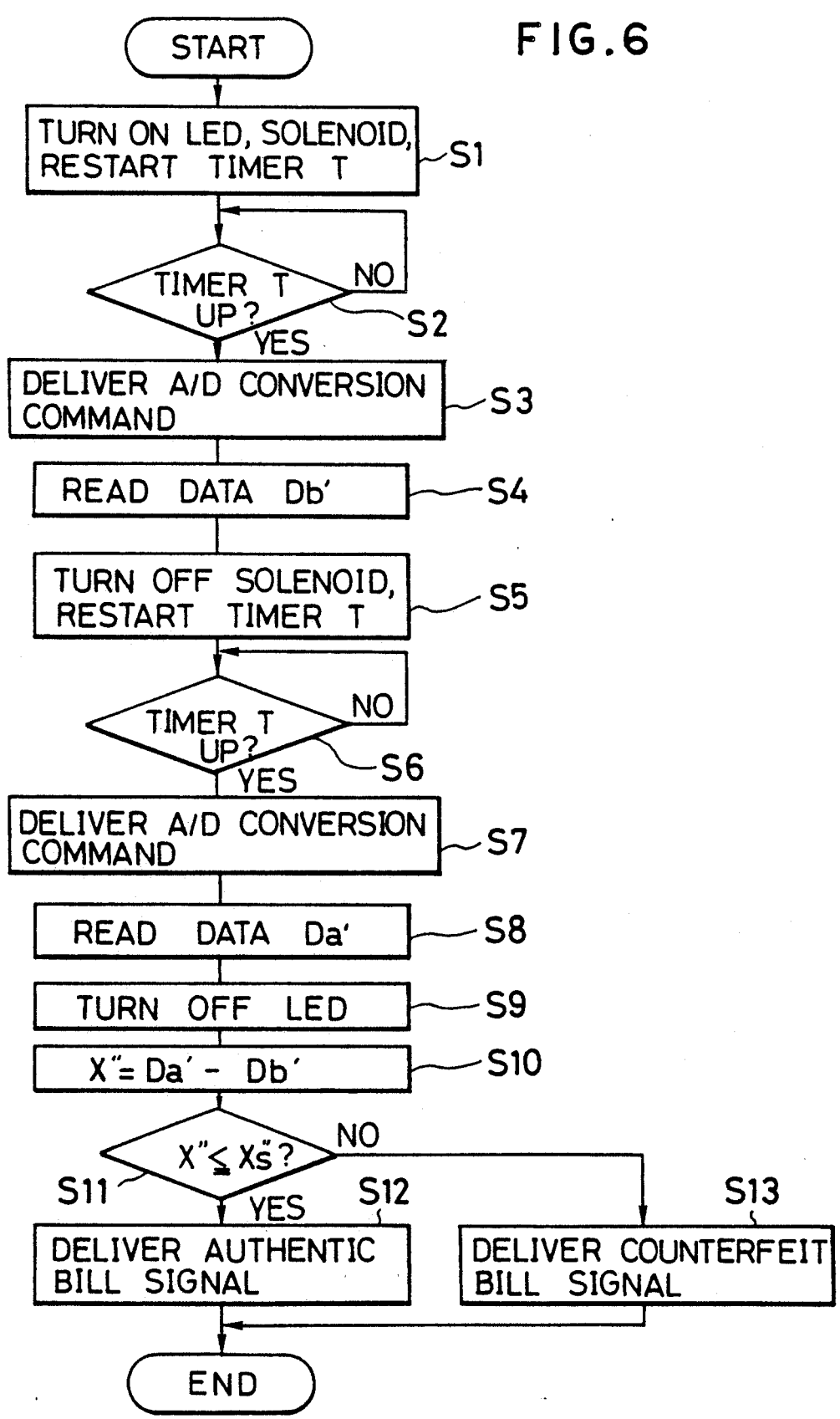
FIG. 6 is a flowchart of a control program executed by a microcomputer of FIG. 5.

With reference to FIGS. 4 to 6, the discriminating apparatus according to a third embodiment of the present invention will be explained.

As compared with the apparatus of the first embodiment, the discriminating apparatus of this embodiment is mainly different in that a combination of a single photodiode and a polaroid filter which is retreatably interposed on a reflected light propagation path is employed in stead of a combination of two photodiodes and a polaroid filter disposed in front of one of the photodiodes.

As shown in FIG. 4, the discriminating apparatus comprises a photodiode 3' for receiving the light which is irradiated from the light-emitting diode 2 onto the bill 1 at an angle $\alpha$ of incidence and reflected therefrom at an angle $\beta$ of reflection and for generating an output current which varies in dependence on an amount of the light received by the same photodiode. The apparatus further comprises a polaroid filter 4', which is fixed to a movable part of a solenoid 9 in such a manner that it is movable between a first position (shown by dotted line in FIG. 4) located in front of the photodiode 3' on the path along which the reflected light is propagated and a second position (shown by the solid line in FIG. 4) away from the propagation path.

As shown in FIG. 5, an output terminal of a current/voltage converter 5', having an input terminal connected to an output terminal of the photodiode 3', is connected to an input terminal of an A/D converter 11 which has an output terminal connected to a central processing unit (not shown) of a microcomputer 13 through a buffer 12 and an input circuit (not shown) of the microcomputer. This micrcomputer 13, preferably constituting part of a control unit of a machine such as an automatic vending machine on which the discriminating apparatus is mounted, further includes a memory, an output circuit, etc. (none of which is illustrated), the output circuit being connected to first and second drive circuits 14, 15 for driving the light-emitting diode 2 and the solenoid 9.

In the following, an operation of the discriminating apparatus of the third embodiment will be explained.

When the bill 1 is delivered to and temporally held at the predetermined position within the discriminating apparatus, as shown in FIG. 4, the microcomputer 13 starts processing of FIG. 6 for discriminating the authenticity of the bill. At first, the micrcomputer 13 drives the solenoid 9 through the second drive circuit 15 so as to cause the polaroid filter 4' to move from the second position shown by the solid line in FIG. 4 to the first position shown by the dotted line, and then causes the light-emitting diode 2 to be turned ON through the first drive circuit 14 and at the same time causes a software timer T to be reset and started (step (S1). As a consequence, the light irradiated from the light-emitting diode 2 and reflected by the bill 1 is received by the photodiode 3' through the polaroid filter 4'. An output current from the photodiode 3', indicative of an amount of the reflected light whose polarized component is eliminated by the polaroid filter 4', is converted into a corresponding voltage in the current/voltage converter 5', and is then applied to the A/D converter 11.

Under these conditions, the microcomputer 13 determines whether or not the timer T is up (step S2). When the timer T is up, that is, when it is determined that the movement of the polaroid filter 4' to the first position is completed and a variation in the output current of the photodiode 3' which occurs with the same movement is fully suppressed, the microcomputer 13 delivers and A/D conversion command to the A/D converter 11 (the step S3). In response to this, the A/D converter 11 converts the analog output voltage of the current/voltage converter 5' into a corresponding digital voltage signal Db' in the form of a predetermined number of bits, and the buffer 12 temporally stores therein the same data Db'. Then, the microcomputer 13 reads out the data Db' from the buffer 12 and causes the memory accommodated in the computer to store the same (step S4), and causes the solenoid 9 to be turned OFF through the second drive circuit 15 and at the same time causes a second software timer T' to be reset and started (step S5).

When the timer T' is up, i.e., when it is determined at the step S6 that the retreat movement of the polaroid filler 4' from the first position shown by the dotted line in FIG. 4 to the second position shown by the solid line is completed and a variation in the output current of the photodiode 3' which occurs with this retreat movement is substantially suppressed, the microcomputer 13 delivers an A/D conversion command to the A/D converter 11 (step S7), and then reads out a data Da' from the buffer 12 and causes the memory to store the same data, which indicates an amount of the reflected light received by the photodiode 3' and containing the polarized component thereof (step S8), and causes the light-emitting diode 2 to be turned OFF through the first drive circuit 14 (step S9).

Subsequently, the microcomputer 13 subtracts the data Db' from the data Ba' to calculate the difference $X''$ (=Da'−Db') therebetween (step S10), and then determines whether or not this difference $X''$ is equal to or less than a value of $Xs''$, which corresponds to the value Vs in the first embodiment (step S11). For the reasons explained in the first embodiment, the difference $X''$ assures a small value for the authentic bill, and a large value for the counterfeit bill. Accordingly, the microcomputer 13 delivers a signal indicative of the authentic bill when the result of determination at the step S11 is affirmative ($X'' \leq Xs''$), whereas it delivers a signal indicative of the counterfeit bill if the determination result is negative (steps S12 and S13). For instance, the microcomputer 13 causes a flat register accommodated therein to store a value of "1" or "0" indicative of the determination result at the step S11, i.e., the authenticity of the bill.

The present invention is not limited to the aforesaid first to third embodiments, and various modifications of these embodiments may be made.

For instance, although a particular color of the light generated by the light source 2 has not been specified in the aforesaid embodiments, the light source 2 may be so arranged as to irradiate light whose color is the complementary color (e.g., red) to the color (e.g., blue) of part of the bill 1 on which the light is irradiated, or is close to the complementary color. In this case, on one hand, a degree of reflection on the surface of the bill 1 scarcely depends on the color of the light generated by the light source 2, and, on the other hand, a degree of reflection of the light, which is complementary in color to the bill, is well absorbed within the bill, so that the reflection degree is reduced. Accordingly, if the light having a color which is the complementary color to the color of the bill or close to the complementary color is irradiated, the difference between the amount of the reflected light, received through the polaroid filter so that a polarized component of the light is eliminated, and the amount of the reflected light, received not though the polaroid filter and containing therein the polarized component, is greatly differentiated between the brilliant counterfeit bill which produces the reflected light containing a large quantity of surface-reflected light (or the polarized component) and the lusterless authentic bill which produces the reflected light in which contribution of the surface-reflected light is small. In this manner, ease of determining the authenticity of the bill is further enhanced by irradiating the complementary color.

In the foregoing embodiments, the authenticity of the bill is determined on the basis of the difference of the amount of the reflected light received when the polaroid filter is disposed on the reflected light propagation path and that received when no filter is disposed, or the ratio of them, the reflected light being reflected on a single part of the bill 1. In other words, the authenticity is determined in accordance with whether or not brilliance of the single part of the bill is coincident with that of the authentic bill. However, a determination may be made as to whether or not a pattern of brilliance of the bill is coincident with such a pattern for the authentic bill, for the determination of the authenticity of the bill. In this case, the difference between or ratio of the aforesaid two kinds of received amounts of light is detected for each of a plurality of parts of the bill, to be compared with a corresponding one of reference values set beforehand, and then the authenticity of the bill is determined on the basis of the results of these comparisons.

Further, each of the aforesaid embodiments is arranged to discriminate a single kind of authentic bill from counterfeit bills, these embodiments may be modified so as to discriminate a plurality of kinds of authentic bills from various counterfeit bills. In this case, at first, the type of an authentic bill thrown is determined in a conventional manner, e.g., by detecting the size of the bill by the use of an appropriate sensor system. Then, in accordance with the result of this determination, a corresponding one of circuit sections, similar in construction to the circuit arrangement shown in FIG. 2 or FIG. 3 and corresponding in number to the types of authentic bills to be discriminated, is connected to associated two light-receiving elements. Alternatively, the aforesaid reference value $Xs''$ at the step S11 of FIG. 6 is set to a value which varies in dependence on the result of the just-mentioned determination.

Although, in the aforesaid embodiments, the cases wherein an authentic bill is discriminated from a counterfeit bill obtained by color-copying the authentic bill have been explained, the present invention also makes it possible to discriminate an authentic bill from various counterfeit bills each having brilliance which is different from that of the authentic bill. Moreover, various types of light sources and light-receiving elements may be used although, in the embodiments, a light-emitting diode and a photodiode are respectively employed as the light source and the light-receiving element.

Although the difference between or the ratio of output currents from two light-receiving elements is compared with a reference value in an analog circuit for the determination of the authenticity of the bill in the first and second embodiments, such determination may be made through digital processing based upon digital data indicative of both the output currents, as in the third embodiment. Moreover, the determination is effected in the third embodiment on the basis of the difference between the output current generated from the light-receiving element when reflected light is received through a polaroid filter and that generated when the reflected light is received not through the filter. However, the determination may be made based upon the ratio of the just-mentioned two kinds of output currents supplied from the light-receiving element, as in the aforesaid second embodiment.

What is claimed is:

1. A method for discriminating authenticity of a bill, comprising steps of:
   (a) irradiating unpolarized light onto the bill at a predetermined angle of incidence;
   (b) detecting an amount of reflected light from the bill, said reflected light containing a polarized component which is produced when the light is reflected on a surface of the bill;
   (c) detecting an amount of the reflected light from which said polarized component is eliminated; and
   (d) detecting a degree of brilliance of the surface of the bill on the basis of the amount of said reflected light detected by said step (b) and that detected by said step (c), to thereby discriminate the authenticity of the bill.

2. A discriminating method according to claim 1, wherein the determination at said step (d) is carried out on the basis of the difference between the amounts of the reflected light respectively detected in said steps (b) and (c).

3. A discriminating method according to claim 2, wherein, in said step (d), said difference is compared with a predetermined reference value, and then a counterfeit bill having a surface whose degree of brilliance is larger than that of an authentic bill is determined when said difference is larger than said predetermined reference value.

4. A discriminating method according to claim 1, wherein the determination at said step (d) is carried out on the basis of the ratio of the amount of the reflected light detected in said step (b) to that detected in said step (c).

5. A discriminating method according to claim 4, wherein, in said step (d), said ratio is compared with a predetermined reference value, and then a counterfeit bill having a surface whose degree of brilliance is larger than that of an authentic bill is determined when said ratio is larger than said predetermined reference value.

6. A discriminating method according to any one of claim 1-5, wherein the light, having a color which is a complementary color of a color of part of the bill on which the light is irradiated or having a color close to the complementary color, is irradiated in said step (a).

7. An apparatus for discriminating authenticity of a bill, comprising:
   a light source for irradiating light onto the bill at a predetermined angle of incidence;
   a first light-receiving element arranged to directly receive reflected light from the bill for generating a first electrical signal which varies in dependence on an amount of the reflected light received by said first light-receiving element;
   a second light-receiving element arranged to receive the reflected light;
   a polaroid filter arranged between the bill and said second light-receiving element on a path along which said reflecting light is propagated, for eliminating a polarized component of the reflected light which is produced when the light is reflected on a surface of the bill, said second light-receiving element being operable to generate a second electrical signal which varies in dependence on an amount of said reflected light received by said second light-receiving element through said polaroid filter; and
   a discrimination means for detecting a degree of brilliance of the surface of the bill on the basis of said first and second electrical signals, to thereby discriminate the authenticity of the bill.

8. A discriminating apparatus according to claim 7, wherein said light source is comprised of a light-emitting diode, and said first and second light-receiving elements are composed of two photodiodes which are formed on a single chip in a manner adjacent to each other.

9. A discriminating apparatus according to claim 7, wherein said discrimination means includes a first circuit for detecting the difference between said first and second electrical signals, and a second circuit for comparing said difference with a reference value.

10. A discriminating apparatus according to claim 9, wherein said discriminating means determines a counterfeit bill having a surface whose degree of brilliance is larger than that of an authentic bill when said difference is larger than said reference value.

11. A discriminating apparatus according to claim 7, wherein said discrimination means includes a first circuit for detecting the ratio of said first electrical signal to said second electrical signal, and a second circuit for comparing said ratio with a reference value.

12. A discriminating apparatus according to claim 11, wherein said discrimination means determines a counterfeit bill having a surface whose degree of brilliance is larger than that of an authentic bill when said ratio is larger than said reference value.

13. A discriminating apparatus according to any one of claims 7-12, wherein said light source irradiates the light, having a color which is a complementary color of a color of part of the bill on which the light is irradiated or having a color close to the complementary color.

14. An apparatus for discriminating authenticity of a bill, comprising:
   a light source for irradiating light onto the bill at a predetermined angle of incidence;
   a light-receiving element for receiving reflected light from the bill for generating an electrical signal which varies in dependence on an amount of the reflected light received by said light-receiving element;
   a polaroid filter arranged to be movable between a first position, located between the bill and said light-receiving element on a path along which said reflected light is propagated, and a second position retreated from said propagation path of said reflected light, said polaroid filter being operable to eliminate a polarized component of the reflected light which is produced when the light is reflected on a surface of the bill;
   drive means for causing said polaroid filter to move between said first and second positions; and
   a discrimination means for detecting a degree of brilliance of the surface of the bill on the basis of said electrical signals generated when said polaroid filter assumes said first and second positions, respectively, to thereby discriminate the authenticity of the bill.

15. A discriminating apparatus according to claim 14, wherein said light source is comprised of a light-emitting diode, and said light-receiving element is composed of a photodiode.

16. A discriminating apparatus according to claim 14, wherein said discrimination means operates to effect the discrimination on the basis of the difference between said electrical signals respectively generated when said polaroid filter assumes said first and second positions.

17. A discriminating apparatus according to claim 14, wherein said discrimination means operates to effect the discrimination on the basis of the ratio of said electrical signal generated when said polaroid filter assumes said first position to said electrical signal generated when said polaroid filter assumes said second position.

18. A discriminating apparatus according to claim 15, wherein said discrimination means includes a first converter for converting an output current of said photodiode into a corresponding voltage, as second converter for converting the output voltage of said first converter into digital data and temporally storing the same data when said polaroid filter assumes either one of said first and second positions, and information processing means for sequentially reading out the digital data from said second converter to calculate one of the difference of these digital data and the ratio of one digital data to the other digital data, and for comparing one of the difference and the ratio with a corresponding reference value.

19. A discriminating apparatus according to claim 18, where in said information processing means determines a counterfeit bill having a surface whose degree of brilliance is larger than that of an authentic bill when one of the difference and the ratio is larger than the corresponding reference value.

20. A discriminating apparatus according to any one of claims 14–19, wherein said light source irradiates the light, having a color which is a complementary color of a color of part of the bill on which the light is irradiated or having a color close to the complementary color.

* * * * *